(12) United States Patent
Birlouez-Aragon

(10) Patent No.: US 6,413,779 B1
(45) Date of Patent: Jul. 2, 2002

(54) METHOD FOR EVALUATING THE HEAT TREATMENT TO WHICH A PROTEINIC NUTRIENT SUCH AS MILK IS SUBJECTED

(75) Inventor: Inès Birlouez-Aragon, Ermont (FR)

(73) Assignee: Institut National Agronomique Paris-Grignon, Paris (FR)

( * ) Notice: Subject to any disclaimer, the term of this patent is extended or adjusted under 35 U.S.C. 154(b) by 0 days.

(21) Appl. No.: 09/147,739

(22) PCT Filed: Aug. 29, 1997

(86) PCT No.: PCT/FR97/01533

§ 371 (c)(1),
(2), (4) Date: Feb. 26, 1999

(87) PCT Pub. No.: WO98/09165

PCT Pub. Date: Mar. 5, 1998

(30) Foreign Application Priority Data

Aug. 30, 1996 (FR) .............................................. 96 10603

(51) Int. Cl.$^7$ .............................................. G01N 33/06
(52) U.S. Cl. ............................. 436/23; 436/20; 436/21; 436/22; 436/23
(58) Field of Search ............................... 436/20–24, 63, 436/177

(56) References Cited

U.S. PATENT DOCUMENTS

| | | | | | |
|---|---|---|---|---|---|
| 4,645,829 A | * | 2/1987 | Ho | .............................. | 530/344 |
| 4,761,368 A | * | 8/1988 | Cerami | .......................... | 435/7 |
| 5,601,079 A | * | 2/1997 | Wong et al. | ................ | 128/633 |
| 5,658,798 A | * | 8/1997 | Bertin et al. | ................... | 436/3 |

FOREIGN PATENT DOCUMENTS

| | | |
|---|---|---|
| EP | 0 343 064 | 11/1989 |
| EP | 0 422 981 | 4/1991 |
| EP | 0 573 054 | 12/1993 |

OTHER PUBLICATIONS

Shuler et al., "Biprocess Engineering Basic Concepts", Prentice Hall, pp. 332–333, 1992.*

Schulman, "Fluorescence and Phosphorescence Spectroscopy: Physiochemical Principles and Practice", Pergamon Press, p. 117, 1977.*

"Heat–Induced Changes In Lactose: Isomerization, Degradation, Maillard Browning", J. O'Brien, Robens Institue of Health & Safety, University of Surrey, Guildford GU2 5XH, UK, International Dairy Federation, Heat Induced changes in milk—Second Edition, pp. 134–170.

Inra Viande, p. 2, Technical Note: Correlation Between Induction Time and Rate of Browning in Heated Model Solutions of Glucose and Lysine, C. Petriella. J. Chirife, Silvia L. Resnik and R. D. Lozano, International Journal of Food Science and Technology (1988) 23, 415–418.

Int. Dair Journal 8 (1998) 771–777, ©1999 Elsevier Science Ltd., "A Rapid Fluorimetric Method to Estimate the Heat Treatment of Liquid Milk", Ines Birlouez–Aragon, Marina Nicolas, Arnaud Metais, Nathalie Marchond, J. Grenier and D. Calvo.

Journal of Agricultural and Food Chemistry, Reprinted from vol. 45, No. 5, pp. 1905–1910, "Degradation of Tryptophan in Heated β–Lactoglobulin–Lactose Mixtures Is Associated with Intense Maillard Reaction", Veronique Moreaux and Ines Birlouez–Aragon.

* cited by examiner

Primary Examiner—Jill Warden
Assistant Examiner—Dwayne K. Handy
(74) Attorney, Agent, or Firm—Jacobson Holman, PLLC

(57) ABSTRACT

The invention concerns a method for evaluating the hot treatment to which a proteinic nutrient such as milk is subjected. It consists in the following steps: a) taking a sample of said nutrient and adding thereto an ionic strength pad and appropriate pH for obtaining a precipitate of proteins denatured by the hot treatment and a transparent supenatant containing proteins which are still soluble; b) analysing the tryptophan present in the supernatant; and c) analysing the fluorescent by-products derived from the advanced Maillard reaction present in the supernatant. The invention is useful in methods for hot treatment of proteinic nutrients.

7 Claims, No Drawings

METHOD FOR EVALUATING THE HEAT TREATMENT TO WHICH A PROTEINIC NUTRIENT SUCH AS MILK IS SUBJECTED

The present invention relates to a new method for evaluating the heat treatment to which a proteinic nutrient such as milk is subjected.

Currently, the specialist in the art has at his disposal some methods for evaluating the heat treatment of milk, two of which are official: the measurement of the lactulose in milks subjected to a U.H.T. process, on the one hand, and the measurement of the beta-lactoglobulin for pasteurised milks on the other hand. These two measurement techniques use high performance liquid chromatography (H.P.L.C.). The first of these methods allows the U.H.T. treatment to be controlled but with a time-lag of at least three hours, which prohibits any rapid intervention on the U.H.T. treatment parameters. The second allows one to appreciate the quality of a pasteurised milk, but likewise with too great a time-lag.

The implementation of these two processes does not allow the manufacturer to intervene rapidly on the current process: a certain literage of milk will therefore have undergone a heat treatment (U.H.T., pasteurisation) under poor conditions, before a correction to the process has been able to be made.

The specialist in the art likewise knows other methods, in particular for measuring the degradation of the proteins such as those present in heated milks. In particular, the products resulting from the Maillard reaction, such as furosine, are measured.

These methods of the prior art, the reliability of which cannot be questioned, present in particular three major disadvantages: as already explained above, they are slow and the results are only known after at least a period of three hours; they only allow a maximum of about twenty samples to be dosaged per day, which is hardly sufficient to follow a continuous process; and they are relatively costly.

Also, one of the aims of the present invention is to provide a method for evaluating the heat treatment to which a proteinic nutrient such as milk is subjected, which allows results to be obtained within short spaces of time compatible with the manufacturers' requirements.

Another aim of the present invention is to provide such a method which permits the measurement of approximately one hundred samples per day.

A supplementary aim of the invention is to provide a method of this type which permits the evaluation of the effect of a heat treatment on the nutritional quality of the proteins of a nutrient such as as those of milk.

These aims, and also others which will be apparent hereinafter, are addressed by a method for evaluating the heat treatment to which a proteinic nutrient such as milk is subjected, which is characterised, according to the present invention, in that it comprises the following steps:

a) taking a sample of said nutrient and adding thereto an ionic strength buffer and of appropriate pH for obtaining on the one hand a precipitate of proteins denatured by the heat treatment and on the other hand a transparent supernatant containing proteins which are still soluble;

b) analysing the tryptophan present in the supernatant; and c) analysing the fluorescent by-products derived from the advanced Maillard reaction present in the supernatant.

Preferably, the tryptophan present in the supernatant is measured by its fluorescence; for example, the measurement is carried out at an excitation wavelength of 290 nm and an emission wavelength of between 330 and 350 nm to obtain a maximum sensitivity. The measurement of the tryptophan could likewise be carried out by its U.V. absorption.

Advantageously, the measurement of the peptide fluorescent by-products derived from the advanced Maillard reaction present in the supernatant is realized with an excitation wavelength of 350 nm and emission wavelength of between 420 and 440 nm to obtain a maximum sensitivity.

So as to show better the conditions of implementation of a method in accordance with the present invention and also its advantages, the specialist in the art should refer to the examples below.

Beforehand, it will be recalled that as a function of the heat treatment, the proteins present in a proteinic nutrient such as milk undergo transformations which allow this heat treatment to be controlled.

In accordance with the present invention, on the one hand tryptophan was selected as marker of the level of denaturation of the proteins and, on the other hand, the fluorescent products derived from the advanced Maillard reaction, which alters the nutritional quality of the protein, as a reflection of the intensity of the reaction between the lysine and the products of carbonyl groups (s) such as sugars and peroxided lipids.

EXAMPLE 1

Milk

A measurement sample is prepared as follows. 500 µl of milk having undergone a heat treatment are mixed with 4500 µl sodium acetate buffer 100 mM at pH 4.6. After vortex agitation, the transparent supernatant is obtained by centrifuging at 9000 revolutions per minute for 10 minutes.

In an acrylic fluorescence tank, 250 µl of supernatant are diluted with 2250 µl water. The fluorescence is measured on a spectrofluorimeter sold under the name Spex by the company Jobin-Yvon or any other equivalent fluorimeter, at the following wavelengths:

excitation wavelength: 290 nm emission wavelength: 340 nm.

The results as a function of various heat treatments are collated in Table I below with those obtained by the traditional methods.

TABLE I

| Measurement method | Trp UR | Invention 100* (PM/Trp) | Furosine (mg/100 g) | βlactoglobulin (mg/L) | Lactulose (mg/L) |
|---|---|---|---|---|---|
| Pasteurised | | | | | |
| average (n = 9) | 2.87 | 14.43 | 9.50 | 2079 | 0 |
| variation-type | 0.90 | 5.78 | 0.93 | 1210 | |
| min/max | 2.5/4.2 | 10.4/18.7 | 7.1/10.4 | 1401/3429 | |

TABLE I-continued

| Measurement method | Trp UR | Invention 100* (PM/Trp) | Furosine (mg/100 g) | βlactoglobulin (mg/L) | Lactulose (mg/L) |
|---|---|---|---|---|---|
| direct UHT | | | | | |
| average (n = 9) | 0.679 | 22.15 | 55.02 | 758 | 138.9 |
| variation/type | 0.137 | 7.37 | 24.22 | 538 | 91.7 |
| min/max | 0.5/0.89 | 16.7/26.6 | 41.5/58.0 | 240/1204 | 72/171 |
| indirect UHT | | | | | |
| average (n = 33) | 0.499 | 40.33 | 160.5 | 89.3 | 568.2 |
| variation-type | 0.160 | 11.71 | 54.1 | 35.4 | 325.3 |
| min/max | 0.17/0.93 | 31.6/45.7 | 132.9/176.2 | 43.4/112.7 | 365.3/597.5 |

Trp: tryptophan
100* PM/Trp: ratio of fluorescence of Maillard products to that of tryptophan.

The fluorescence of tryptophan (Trp) is strongly correlated (r=0.98) to the concentration of the β-lactoglobulin, a reference method to characterise pasteurised milk. It thus permits a very rapid differentiation between a pasteurised milk and a UHT milk.

The ratio between the fluorescence of the Maillard products (PM) over the fluorescence of tryptophan (100* PM/Trp) constitutes a global thermal index which likewise causes this other reaction to occur which is essentially present in UHT milk, especially of the indirect type. This is in fact correlated to furosine (r=0.82) and is inversely proportional to the nutritional quality (content of essential lysine acid/amine) of the heated milk proteins.

These two measurements together provide rapid information concerning the type of heat treatment undergone by the milk and the quality of this treatment.

Owing to the speed of this process one can, on the one hand, measure one hundred samples per day and, on the other hand, one can act quickly so as to permit the production of a milk

EXAMPLE 2

Soya

The present method can also be used to evaluate the degree of torrefaction of soya.

Grains are collected on torrefaction and are crushed finely to flour. The flour (500 mg) is then delipidated by the addition of 10 ml petroleum ether. After vortex mixing, the organic phase is cast to one side and the operation is repeated once. The flour is dried in an evaporator under vacuum.

The solubilisation of the proteins is carried out by the addition of borate buffer 100 mM at pH 8.0, as described in the article by Bush RF, Toullec R, Caugant I, Guilloteau P, Effect of raw pea flower on nutrients digestiblity and immune responses in the pre-ruminant calf. J.Dairy Sci. 1992, 75:3539–3552. A centrifuging of 10 mn at 9000 revolutions per minute allows the transparent soluble proteins to be separated.

The reading is carried out as previously by diluting the transparent supernatant 20 times in water (namely 150 μl plus 2850 μ water) in an acrylic fluorescence tank.

In Table II below, results comprising two heat treatments are collated: flour heated in a water bath and grains heated in a torrefier. The measurements on the soya treated in the water bath are carried out on samples prepared according to the same method.

The spectrofluorimeter reading is carried out under the same conditions as in Example 1.

TABLE II

| | Duration (min) of heating at 160° C. | | | | |
|---|---|---|---|---|---|
| | 5 | 10 | 15 | 20 | 25 |
| flour (water bath) | | | | | |
| soluble proteins (g/L) | 0.9 | 0.15 | 0.22 | 0.12 | 0.054 |
| Trp (UR) | 12.9 | 3.95 | 4.47 | 3.29 | 2.74 |
| 100μ (PM/TrpP) | 14.8 | 78.5 | 96.5 | 130.7 | 215.7 |
| Grain (torrefier) | | | | | |
| soluble proteins (g/L) | 6.44 | 1.78 | 1.06 | 0.83 | 0.81 |
| Trp (UR) | 78.30 | 18.90 | 10.92 | 0.93 | 0.91 |
| 100* (PM/Trp) | 17.1 | 49.3 | 135.8 | 236.5 | 326.9 |

Trp: tryptophan
100* (PM/TrpP): ratio of the fluorescence of the Maillard products to that of tryptophan The fluorescence of the tryptophan of the transparent supernatant is a rapid measurement of the concentration of soluble, weakly denatured proteins and is very strongly correlated to the dosage of proteins (Kjeldahl or Biuret's calorimetric method; r=0.99). The Maillard fluorescent products are formed here from lipid peroxides.

It can be seen from the present example that the torrefaction of the grain degrades the soya proteins much more strongly than a treatment of the flour in a water bath, despite identical temperatures. Solely the analysis of the soluble proteins, which is longer and more costly, would not allow these conclusions to be drawn.

This example therefore shows the necessity to carry out the torrefaction in the best possible conditions, hence the importance of using a control method which is as quick and precise as possible, such as that in accordance with the present invention.

EXAMPLE 3

Maize

The present method can likewise serve to evaluate the intensity of drying of maize grains, drying being a particular form of heat treatment. This drying intensity has an influence on the quality and the extraction yield of starch. an influence on the quality and the extraction yield of starch.

Currently, this drying intensity is measured by the turbidity of the solution of denatured proteins.

In accordance with the present invention, dried maize grains are collected, crushed into flour and the latter is solublised in a solution of sodium chloride (NaCl) at 5%. Then centrifuging is carried out according to the procedure defined by the Institut Technique des Céréales et des Fourrages (I.T.C.F.).

The results obtained are collated in Table III by comparison with the traditional method set out above.

TABLE III

| Drying temperature | Ambient temperature | 90° C. | 110—120° C. |
|---|---|---|---|
| turbidity | 4% | 47% | 66% |
| Trp (UR) | 6.04 | 3.91 | 2.90 |

The low content of reducing sugars or unsaturated liquids in the maize grain does not allow a measurement of the information on the denaturation of the proteins under heat by analysing the concentration of proteins still soluble in the NaCl buffer.

The method in accordance with the present invention therefore permits, on the one hand, a control of the heat treatment to which a milk or a proteinic nutrient is subjected and even to determine it subsequently and, on the other hand, permits a definition of the nutritional quality of the nutrient which is analysed.

What is claimed is:

1. A method for evaluating loss of nutritional quality of proteins contained in a nutrient subjected to a heat treatment comprising the following steps:
    a) collecting a sample of said nutrient subjected to said heat treatment and adding thereto an ionic strength buffer at appropriate pH to obtain, on the one hand, a precipitate of proteins denatured by said heat treatment and, on the other hand, a transparent supernatant containing proteins which are still soluble;
    b) analyzing tryptophan fluorescence in said supernatant as a measure of protein denaturation and tryptophan degradation consecutive to said heat treatment;
    c) analyzing fluorescent by-products derived from an advanced Maillard reaction in said supernatant;
    d) calculating the ratio between the fluorescence of Maillard products over the fluorescence of tryptophan; and
    e) correlating said ratio between the fluorescence of Maillard products over the fluorescence of tryptophan to the amount of nutritional damage on lysine.

2. A method for evaluating loss of nutritional quality of proteins contained in a nutrient subjected to a heat treatment consisting essentially of the following steps:
    (a) collecting a sample of said nutrient subjected to said heat treatment and adding thereto an ionic strength buffer at appropriate pH to obtain, on the one hand, a precipitate of proteins denatured by said heat treatment and, on the other hand, a transparent supernatant containing proteins which are still soluble;
    (b) analyzing tryptophan fluorescence in said supernatant as a measure of protein denaturation and tryptophan degradation consecutive to said heat treatment;
    (c) analyzing fluorescent by-products derived from an advanced Maillard reaction in said supernatant;
    (d) calculating the ratio between the fluorescence of Maillard products over the fluorescence of tryptophan; and
    (e) correlating said ratio between the fluorescence of Maillard products over the fluorescence of tryptophan to the amount of nutritional damage on lysine.

3. The method of claim 1, wherein said analysis of said tryptophan and said Maillard reaction products is carried out at an excitation wavelength of 290 nm and an emission wavelength of between 330 and 350 nm.

4. The method of claim 1, wherein said analysis of said fluorescent protein by-products derived from said advanced maillard reaction present in said supernatant is carried out at an excitation wavelength of 350 nm and an emission wavelength of between 420 and 440 nm.

5. The method of claim 1, wherein said nutrient is milk.

6. The method of claim 1, wherein said nutrient is soya.

7. The method of claim 1, wherein said nutrient is maize.

* * * * *